(12) United States Patent
Aydogan et al.

(10) Patent No.: US 9,107,895 B2
(45) Date of Patent: Aug. 18, 2015

(54) METHODS AND COMPOSITIONS FOR IMAGING CANCER CELLS

(75) Inventors: Bulent Aydogan, Orland Park, IL (US); Tijana Rajh, Argonne, IL (US)

(73) Assignees: The University of Chicago, Chicago, IL (US); UChicago Argonne, LLC, Chicago, IL (US)

( * ) Notice: Subject to any disclaimer, the term of this patent is extended or adjusted under 35 U.S.C. 154(b) by 303 days.

(21) Appl. No.: 12/843,664

(22) Filed: Jul. 26, 2010

(65) Prior Publication Data

US 2011/0020243 A1 Jan. 27, 2011

Related U.S. Application Data

(60) Provisional application No. 61/228,481, filed on Jul. 24, 2009.

(51) Int. Cl.
| | | |
|---|---|---|
| *C07H 23/00* | (2006.01) | |
| *A61K 33/24* | (2006.01) | |
| *A61K 31/7135* | (2006.01) | |
| *A61K 49/00* | (2006.01) | |
| *A61K 9/14* | (2006.01) | |
| *A61K 49/04* | (2006.01) | |
| *A61P 43/00* | (2006.01) | |
| *A61K 31/7004* | (2006.01) | |
| *B82Y 5/00* | (2011.01) | |

(52) U.S. Cl.
CPC ............. *A61K 33/24* (2013.01); *A61K 31/7004* (2013.01); *A61K 49/0485* (2013.01); *B82Y 5/00* (2013.01); *C07H 23/00* (2013.01)

(58) Field of Classification Search
None
See application file for complete search history.

(56) References Cited

U.S. PATENT DOCUMENTS

| | | | | |
|---|---|---|---|---|
| 6,818,199 | B1 * | 11/2004 | Hainfeld et al. | 424/1.11 |
| 2003/0082720 | A1 * | 5/2003 | Lifton et al. | 435/69.1 |
| 2005/0136001 | A1 * | 6/2005 | McBride et al. | 424/1.11 |
| 2006/0148124 | A1 * | 7/2006 | Wilson | 438/82 |
| 2007/0007511 | A1 * | 1/2007 | Choi et al. | 257/40 |
| 2010/0034735 | A1 | 2/2010 | Chen et al. | 424/1.29 |
| 2011/0110868 | A1 * | 5/2011 | Akhtari et al. | 424/9.322 |

FOREIGN PATENT DOCUMENTS

WO WO 2004/112590 12/2004

OTHER PUBLICATIONS

Aydogan et al., "AuNP-DG: Deoxyglucose-labeled gold nanoparticles as x-ray computed tomography contrast agents for cancer imaging," *Mol. Imaging Biol.*, 12(5):463-7, 2010.
Bonvento et al., "CT Angiography With Gadolinium-Based Contrast Media," *Acad. Radiol.*, 13(8):979-85, 2006.

(Continued)

*Primary Examiner* — Peter J Reddig
*Assistant Examiner* — Sarah Chickos
(74) *Attorney, Agent, or Firm* — Norton Rose Fulbright US LLP

(57) ABSTRACT

Disclosed are compositions comprising nanoparticles and uses thereof. Such nanoparticles include gold nanoparticles conjugated to glucose or a glucose derivative, which are useful as contrast agents in imaging methods such as computed tomography (CT). Nanoparticles disclosed herein are useful in imaging various cells, tissues, and organs, and are particularly useful in imaging tumors and tumor cells in vitro and in vivo.

10 Claims, 13 Drawing Sheets

(56) References Cited

OTHER PUBLICATIONS

Cai et al., "Colloidal gold nanoparticles as a blood-pool contrast agent for X-ray computed tomography in mice," *Invest. Radiol.*, 42:797-806, 2007.

Fruman et al., "Perfluoroctyl bromide as a blood pool contrast agent for computed tomographic angiography," *Acad. Radiol.*, 1:151-3, 1994.

Gao et al., "In vivo cancer targeting and imaging with semiconductor quantum dots," *Nat. Biotechnol.*, 22(8):969-976, 2004.

Hainfeld et al., "Gold nanoparticles: a new X-ray contrast agent," *Br. J. Radiol.*, 79(939):248-253, 2006.

Hainfeld et al., "Radiotherapy enhancement with gold nanoparticles," *J. Pharm. Pharmacol.*, 60(8):977-85, 2008.

Hainfled et al., "Gold nanoparticles enhance the radiation therapy of a murine squamous cell carcinoma," *Phys. Med. Biol.*, 55(11):3045-59, 2010.

Hayat, In: *Colloidal gold: Principles, Methods and Applications*, vol. 3, San Diego, Academic Press, 1991.

Hayat, In: *Colloidal Gold: Principles, Methods and Applications*. vol. 1, San Diego, Academic Press, 1989.

Jain et al., "Iron oxide nanoparticles for sustained delivery of anticancer agents," *Mol. Pharm.*, 2(3):194-205, 2005.

Kao et al., "Long-residence-time nano-scale liposomal iohexol for X-ray-based blood pool imaging," *Acad. Radiol.*, 10(5):475-83, 2003.

Kim et al., "Antibiofouling polymer-coated gold nanoparticles as a contrast agent for in vivo x-ray computed tomography imaging," *J. Am. Chern. Soc.*, 129:7661-65, 2007.

Li et al., "A novel functional CT contrast for molecular imaging of cancer," *Phys. Med. Biol.*, 55(15):4389-4397, 2010.

Miyamoto et al., "Development of water-soluble metallofullerenes as X-ray contrast media," *Em. Radiol.*, 16:1050-3, 2006.

Popovtzer et al., "Targeted gold nanoparticles enable molecular CT imaging of cancer," *Nano Lett.*, 8(12):4593-4596, 2008.

Qian et al., "In vivo tumor targeting and spectroscopic detection with surface-enhanced Raman nanoparticle tags," *Nat. Biotechnol.*, 26:83-90, 2008.

Rabin et al., "An X-ray computed tomography imaging agent based on long-circulating bismuth sulphide nanoparticles," *Nat. Mater.*, 5:118-22, 2006.

Rahman et al., "Enhancement of radiation effects by gold nanoparticles for superficial radiation therapy," *Nanomedicine*, 5(2):136-42, 2009.

Schmiedl et al., "CT blood pool enhancement in primates with lopromide-carrying liposomes containing soy phosphatidyl glycerol," *Acad. Radiol.*, 6:164-9, 1999.

Slot and Geuze, "A new method of preparing gold probes for multiple-labeling cytochemistry," *Em. J. Cell Biol.*, 38:87-93, 1985.

Su et al., "Monitoring tumor glucose utilization by positron emission tomography for the prediction of treatment response to epidermal growth factor receptor kinase inhibitors," *Clin. Cancer Res.*, 12:5659-67, 2006.

Vera and Mattrey, "A molecular CT blood pool contrast agent," *Acad. Radiol.*, 9:784-92, 2002.

Weissleder, "Molecular imaging in cancer," *Science*, 312:1168-71, 2006.

Yu and Watson, "Metal-Based X-ray Contrast Media," *Chem. Rev.*, 99:2352-78, 1999.

Zhang et al., "Enhanced radiation sensitivity in prostate cancer by gold-nanoparticles," *Clin. Invest. Med.*, 31(3):E160-7, 2008.

* cited by examiner

METHODS AND COMPOSITIONS FOR IMAGING CANCER CELLS

This application claims the priority benefit of U.S. Application No. 61/228,481, filed Jul. 24, 2009, which is specifically incorporated herein by reference in its entirety without disclaimer.

BACKGROUND OF THE INVENTION

1. Field of the Invention

The invention relates generally to the fields of contrast agents for use in imaging and nanoparticles. In certain aspects, gold nanoparticles attached to glucose or a glucose derivative, such as 2-Deoxy-D-Glucose (2-DG), are provided. Such nanoparticles are particularly useful as a contrast agent in imaging, such as computed tomography (CT) or X-ray imaging.

2. Description of Related Art

To accurately stage and treat malignancies, precise knowledge of tumor location, size, and lymphatic or distant spread is essential. In the context of radiation therapy, the advent of highly conformal techniques—such as three-dimensional conformal radiotherapy (3D-CRT), intensity modulated radiotherapy (IMRT) and image guided radiotherapy (IGRT)—has escalated the need for more accurate target visualization and delineation based on anatomic and physiological images. While imaging with computed tomography (CT), magnetic resonance imaging (MRI) and ultrasound imaging (US) provides valuable anatomical information, all lack the high sensitivity and specificity offered by a functional imaging modality such as positron emission tomography (PET) or single photon emission computed tomography (SPECT). However, despite the ability of PET and SPECT to detect functional processes in the body, they suffer from relatively poor spatial resolution compared to many anatomic imaging modalities such as CT. Also, PET imaging has several drawbacks including the production, transportation, and cost of the radiopharmaceuticals, which limit wider use of this technology. Moreover, PET images do not provide anatomical information, and are therefore inadequate for radiation or surgical treatment planning. The recent development of hybrid PET-CT scanners and sophisticated image registration algorithms allows for combined image sets from CT and PET to be used in the diagnosis and staging of malignant diseases. However, despite the benefits of combined PET-CT, the full potential of CT imaging cannot be utilized because the superb spatial resolution provided by CT scans is not shared by the PET images. For instance, current PET technology has limitations in detecting tumors of fewer than $10^9$ cells (approximately 1 cm in diameter) (Weissleder, 2006). That shortcoming has significance for the early diagnosis of cancer, where small malignant lesions can be missed by PET scans.

In the last decade, studies have demonstrated that CT imaging can, when combined with an X-ray contrast agent, offer both anatomical and functional data (Lee, 2002). However, this technique, termed functional CT, has not gained widespread clinical use because of the limitations of current contrast agents. To date, the most commonly used X-ray contrast agents are iodine-based compounds. Despite their clinical use, iodine-based contrast agents have several drawbacks including a high osmolality and a short blood half-life (less than 10 min) that requires imaging immediately after administration. Also, iodine has a moderate atomic number (Z) that limits the level of achievable CT contrast, decreasing its usefulness in radiation therapy planning, which relies almost exclusively on such values. More importantly, commercially available iodine-based X-ray contrast agents lack tumor-specific targeting ability. Conjugates with targeting moieties, such as antibodies, fail to deliver iodine to disease sites at a concentration detectable by current CT scanners. In addition to iodine-based agents, several other experimental X-ray contrast materials have been tested with varying degrees of success (Kao et al., 2003; Schmiedl et al., 1999; Froman et al., 1994); Vera and Mattrey, 2002). However, the development of intravascular X-ray contrast agents based on other mid-Z to high-Z materials, especially those agents with tumor-specific targeting capability, has not been successful due to performance, cost, and toxicity issues (Bonvento et al., 2003; Miyamoto et al., 2006; Yu and Watson, 1999).

Thus, there remains a need for improved contrast agents for use in CT and X-ray imaging, and there is a particular need for contrast agents with tumor-specific targeting ability to serve as a means of functional and/or molecular imaging of cancer. Some studies have investigated the feasibility of using various materials at the nanometer scale (Rabin et al., 2006; Qian et al., 2008; Popvtzer et al., 2008; Cai et al., 2007; Kim et al., 2007; Hainfeld et al., 2006). Gold nanoparticles (AuNPs) may offer advantages over iodine-based compounds. For example, gold attenuates X-rays more effectively than iodine, and thus produces superior contrast. Also, AuNPs may have a longer biological half-life than iodine-based compounds. For these reasons, studies have investigated the use of AuNPs as an X-ray contrast agent, including attempts to target tumor cells using an antibody or other such moiety (Hainfeld et al., 2006; Popvtzer et al., 2008; Gao et al., 2004; Jain et al., 2005; Zhang et al., 2008). Although thioglucose-conjugated AuNPs have been reported as useful for treating cancer (US. Pub. No. 2010/0034735), it remains unknown whether such AuNPs could be used as contrast agents to successfully image tumors using techniques such as CT or X-ray imaging.

SUMMARY OF THE INVENTION

Compositions and methods directed to nanoparticles and contrast agents for imaging are provided. In some aspects, there are gold nanoparticles (AuNPs) attached directly or indirectly (through a linker, particularly a functional one such as PEG) to a glucose derivative. In particular embodiments, gold nanoparticles are attached directly or indirectly to 2-Deoxy-D-Glucose (2-DG). In some aspects, gold nanoparticles are attached directly to 2-Deoxy-D-Glucose, and these AuNPs are referred to herein as AuNP-DG. In certain aspects, the AuNP-DG particles are efficiently taken up by tumor cells and increase the imaging contrast of tumor cells as compared to surrounding non-tumor tissue. In some embodiments, AuNP-DG is a useful metabolic functional contrast agent for imaging, such as CT or X-ray imaging.

In some aspects, there is provided a composition comprising two or more parts. One part is a nanoparticle comprising a chemical element. In certain aspects, the chemical element has an atomic number of 70 or greater. In other aspects, the chemical element has an atomic number of 75 or greater. In some embodiments, the atomic number is 79, which is the atomic number of gold. In other aspects, the chemical element has a molecular weight greater than 100 Daltons, a molecular weight greater than 150 Daltons, or a molecular weight greater than 190 Daltons. The second part comprises a tumor-targeting molecule that is attached to the nanoparticle. In certain embodiments, the tumor-targeting molecule increases uptake of the nanoparticles by cancer cells (or tumor cells) relative to non-cancer (or non-tumor) cells. As used herein, a "cancer cell" or "tumor cell" is a cell that cannot respond properly to one or more internal or external growth inhibitory stimuli. A tumor includes tumor cells or cancer cells.

A "nanoparticle" as used herein refers to a particle having a particle size on the nanometer scale, generally less than 1 micrometer. In one embodiment, the nanoparticle has a particle size up to about 50 nm. In another embodiment, the nanoparticle has a particle size up to about 10 nm. In some embodiments, the nanoparticle has a particle size greater than 3 nm, or a particle size of about 3 nm to about 9 nm. In particular embodiments, the nanoparticle has a particle size of about 3, 4, 5, 6, 7, 8, 9, 10, 11, 12, 13, 14, 15, 16, 17, 18, 19, 20, or more nm, or any size derivable therein. The nanoparticle may include molecules, molecular groups, chemical elements, compounds, and the like attached to the nanoparticle. A nanoparticle attached to glucose or a glucose derivative may have a mean hydrodynamic diameter, as measured by dynamic light scattering techniques, of less than about 10 nm, between about 7 and about 9 nm, or about 8 nm. In some aspects, a nanoparticle attached to a glucose derivative, such as 2-Deoxy-D-Glucose, has a mean hydrodynamic diameter of about 4, 5, 6, 7, 8, 9, or 10, 20, 30, 40, 50 or more nm, or any diameter derivable therein. In certain embodiments, a nanoparticle attached to 2-Deoxy-D-Glucose has a mean hydrodynamic diameter of about 8 nm.

In certain aspects, a chemical element is included in compositions disclosed herein. Such a chemical element may be a metal. Metals useful in some embodiments include, but are not limited to, iron (Fe), chromium (Cr), aluminum (Al), gallium (Ga), indium (In), hafnium (Hf), tin (Sn), zirconium (Zr), molybdenum (Mo), titanium (Ti), vanadium (V), cobalt (Co), nickel (Ni), copper (Cu), yttrium (Y), tantalum (Ta), tungsten (W), lead (Pb), boron (B), niobium (Nb), germanium (Ge), praseodymium (Pr), uranium (U), cerium (Ce), erbium (Er), neodymium (Nd), magnesium (Mg), calcium (Ca), barium (Ba), strontium (Sr), gold (Au), silicon (Si), bismuth (Bi), palladium (Pd), silver (Ag), platinum (Pt), and combinations thereof. In some embodiments, the chemical element is a metal having a molecular weight (or atomic weight) greater than 100 Daltons, such as gold, bismuth, palladium, silver, tin, barium, tungsten, platinum, lead, or uranium. In certain aspects, the chemical element comprises gold, which has a molecular weight of approximately 197. In other aspects, the chemical element comprises bismuth, which has a molecular weight of approximately 209.

In some aspects, a tumor-targeting molecule is directly or indirectly attached to a nanoparticle. A tumor-targeting molecule is any molecule that is more readily taken up by tumor cells than by non-tumor cells. A tumor-targeting molecule may be a chemical, a chemical group, a compound, an antibody, a nucleic acid, a peptide, a polypeptide, or the like. In some embodiments, the tumor-targeting molecule is a molecule, molecular group, or a compound. In certain aspects, the tumor-targeting compound is glucose or a glucose derivative. Glucose molecules useful in some embodiments include D-glucose and L-glucose. A glucose derivative refers to a molecule derived from glucose and includes any molecule derived from glucose, including any of the examples of glucose derivatives provided herein. Non-limiting examples of glucose derivatives include deoxyglucose, 2-Deoxy-D-Glucose, alpha-D-glucopyranose, beta-D-glucopyranose, 3-phospho-D-glycerate, alpha-D-glucose-1-phosphate, alpha-D-glucose-6-phosphate, beta-D-glucose-6-phosphate, beta-D-glucuronate, beta-D-glucosamine, beta-D-glucosamine-6-phosphate, D-glucosamine-6-phosphate, D-glucosamine, D-glucosaminide, D-glucosaminyl-D-glucosaminide, glucose-1,6-bisphosphate, glucose-1-phosphate, glucose-6-phosphate, and others known to those in the art. In certain aspects, the glucose derivative is deoxyglucose or 2-Deoxy-D-Glucose. In specific embodiments, a glucose derivative is attached directly to the nanoparticle. In other embodiments, a glucose derivative is attached indirectly to the nanoparticle, which means that another chemical moiety is attached directly to the nanoparticle and to the glucose derivative.

Compositions may further include a biocompatible polymer, such as a polyether compound. A non-limiting example of a polyether compound is polyethylene glycol (PEG). It is specifically contemplated that embodiments include a AuNP-DG comprising PEG. Also included are compositions comprising derivatives of PEG including monomethoxypolyethylene glycol (mPEG). In some aspects, the PEG molecules have an average molecular weight between about 100 and about 20,000 Daltons, or between about 500 and about 15,000 Daltons, or between about 1,000 and about 5,000 Daltons, or any range derivable therein. In certain aspects, PEG molecules are attached to a nanoparticle, such as a gold nanoparticle. For example, PEG-sulfhydryl molecules (PEG-SH) or methoxy-PEG-sulfhydryl (methoxy-PEG-SH) molecules may be attached to a nanoparticle, such as a gold nanoparticle. In some aspects, the nanoparticle contains PEG-SH or methoxy-PEG-SH molecules that terminate with mercapto (or —SH) groups on both ends. In other aspects, the PEG-SH or methoxy-PEG-SH molecules contain a carboxyl group, with the carboxyl group being at the opposite end of the molecule as the mercapto group. For example, regarding such a molecule, the mercapto group may attach the PEG or methoxy-PEG molecule to a nanoparticle, such as a gold nanoparticle, while the carboxyl group attaches to glucose or a glucose derivative. In some aspects, the glucose derivative attached to a nanoparticle, such as a gold nanoparticle, via a PEG molecule is 2-Deoxy-D-glucose. It is contemplated that any embodiment involving AuNP-DG may involve an AuNP-DG comprising PEG. Also contemplated are methods and compositions that specifically exclude AuNP-DG comprising PEG.

In some embodiments, a composition comprises a gold nanoparticle and glucose or a glucose derivative that is attached to the gold nanoparticle. For example the glucose or glucose derivative may be conjugated to the nanoparticle. In such a composition, the glucose or glucose derivative may be, for example, deoxyglucose or 2-Deoxy-D-Glucose. In certain aspects, the glucose derivative may be attached to the gold nanoparticle at the 2-Carbon site of the 2-Deoxy-D-Glucose. In other embodiments, the glucose derivative is attached to the gold nanoparticle at the 1-Carbon, 3-Carbon, or other such position. In a particular embodiment, 2-Deoxy-D-Glucose is attached to a gold nanoparticle at the 2-Carbon site of the 2-Deoxy-D-Glucose.

Attachment of a molecule, such as glucose or a glucose derivative, to a nanoparticle may be via a linker group. Such a linker group may be a mercapto group, which is also known as a thiol group or —SH group. For example, one or more 2-Deoxy-D-Glucose molecules may be attached to a nanoparticle via a mercapto group that is present at the 2-Carbon position of the 2-Deoxy-D-Glucose. In certain aspects, one or more than one glucose or glucose derivative is attached to the nanoparticle. For example, between five and ten 2-Deoxy-D-Glucose molecules may be attached to a nanoparticle. In some embodiments, a composition comprises a plurality of gold nanoparticles and a plurality of glucose or glucose derivatives attached to at least one of the plurality of gold nanoparticles, the plurality of glucose or glucose derivatives comprising at least one of glucose or a glucose derivative.

Compositions and methods disclosed herein may also include a solvent. For example, a plurality of gold nanoparticles and a plurality of glucose or glucose derivatives may be disposed in the solvent. Such a solvent includes any suitable solvent known in the art. In certain aspects, the solvent includes water. The solvent may include saline, and, in some embodiments, the solvent is phosphate-buffered saline. In certain aspects, a composition is in a pharmaceutically acceptable formulation.

Certain compositions are suitable for use in imaging techniques, and certain methods include the use of imaging. Types of imaging techniques contemplated include X-ray imaging, computed tomography (CT), magnetic resonance imaging (MRI), magnetic resonance spectroscopy (MRS) optical imaging, optical coherence tomography, positron emission tomography (PET), single photon emission computed tomography (SPECT), or combinations thereof. In some aspects, use of one or more imaging techniques is specifically excluded. For example, in some embodiments, the use of MRI, MRS, PET, or SPECT imaging is excluded. In certain embodiments, the use of PET imaging is excluded.

In some embodiments, compositions are configured for use with a CT scanner. For example, compositions may be configured such that if the composition is imaged with a CT scanner, at least some portion of the imaged voxels of the composition will have an imaged intensity of greater than that of normal tissue, i.e., greater than 20-100 Hounsfield Units (HU). As used herein, a "voxel" (or volumetric pixel) refers to a volume element, representing a value on a regular grid in three dimensional space. A "Hounsfield unit" (HU) refers to the numeric information contained in each pixel or voxel of an image, such as a CT image. In an image, such as a CT image, the HU value reflects the density of the tissue or the intensity of a reporter molecule. A higher HU value correlates with increased contrast. In certain aspects, a composition is configured such that if the composition is imaged with a CT scanner, at least some portion of imaged voxels of the composition will have an imaged intensity that is different than that of normal and cancerous tissue. For example, the imaging intensity may be greater than 100 HU, greater than 300 HU, greater than 600 HU, between 800 and 1000 HU, or greater than 1000 HU. In certain aspects, at least some portion of the imaged voxels will have an imaged intensity of greater than 10, 20, 30, 40, 50, 60, 70, 80, 90, 100, 200, 300, 400, 500, 600, 700, 800, 900, 1000, or 1100 HU, or any intensity value derivable therein that differentiates the tumor from the surrounding normal tissue.

For some embodiments, a composition is useful for imaging one or more tumors. It is contemplated that any tumor known in the art may be imaged using compositions and methods disclosed herein, such as tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, uterus, prostate, testicle, ovary, skin, head, neck, esophagus, bone marrow, and other tissues. In certain aspects, a composition is configured such that if the composition is injected into a subject having one or more tumors comprising cancer cells, the cancer cells will absorb at least a portion of the gold nanoparticles. In addition, in certain embodiments, if at least one of the one or more tumors are imaged with a CT scanner after the cancer cells of the tumor absorb gold nanoparticles, at least some portion of the imaged voxels of the tumor will have an imaged intensity greater than that of normal and cancerous tissue, i.e., greater than 20-100 HU. In certain aspects, the imaged intensity is greater than 1000 HU. In certain aspects, at least some portion of a tumor has an image intensity of greater than that of normal tissue, such as greater than 10, 50, 100, 300, 600, 800, 1000, 1500, 2000, 2500, 3000, 3500, 4000, 4500, or more HU, or any intensity value derivable therein that differentiates the tumor from the surrounding normal tissue.

In some embodiments, a method is provided where imaging data is collected after administration of any compound disclosed herein, the imaging data is reviewed, and a treatment decision is made based on the imaging data. The treatment decision may be to administer a therapy or not to administer a therapy. Also contemplated are methods where a subject is imaged after a composition disclosed herein is administered to the subject, and a treatment is then administered to the subject subsequent to the imaging.

Also contemplated are kits comprising one or more compositions disclosed herein and kits useful for methods disclosed herein. For example, a kit may include a container having a sterile reservoir that houses any composition disclosed herein. A kit may also include instructions for administering the composition to a subject, such as prior to collecting imaging data of the subject with penetrating radiation.

In certain aspects, methods disclosed herein are directed to one or more subjects, or compositions disclosed herein are formulated for administration to a subject. As used herein, a "subject" includes any organism, such as an animal or human. It is contemplated that methods disclosed herein may also be practiced on a portion of a subject, such as the brain, tissue, an organ, a limb, or a biological sample. A biological sample is a sample that contains biological material such as all or part of an organ, tissue, cells, nucleic acids, proteins, or other such macromolecules and substances. In certain aspects, the subject is suffering from a disease, condition, or injury. In other aspects, the subject is at risk for developing, or is being treated for, a disease, condition, or injury. Such a disease may be a neoplastic disease, such as cancer, or may be any other abnormal condition of an organism that impairs health. In certain aspects, the subject is suspected of having cancer, has been diagnosed with cancer, is at risk of developing cancer, and/or is being treated for cancer. The cancer may be benign or malignant, and the subject may have one or more tumors in one or more tissues or organs. In certain embodiments, the tumor is a solid tumor.

There are provided methods comprising administering a composition disclosed herein to a subject. For example, a composition may be administered to the subject to prepare the subject for imaging. In certain aspects, the composition is administered to the subject prior to imaging. The composition may be administered to the subject immediately prior to imaging or may be administered 5 minutes, 10 minutes, 20 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, or more, or any number of hours derivable therein, prior to imaging.

In some embodiments, there is provided a method of imaging at least a portion of a subject. In certain aspects, such a method includes collecting imaging data of a subject with penetrating radiation after any of the compositions disclosed herein have been administered to the subject. For example, gold nanoparticles conjugated to glucose or a glucose derivative may be administered to a subject prior to imaging the subject with an imaging technique that uses penetrating radiation, such as X-ray imaging or CT imaging. In certain aspects, imaging data is collected and used to generate one or more images. The one or more images may be displayed in a form perceivable by a user, such as an image displayed on a computer monitor or other digital output device. In certain embodiments, a subject or portion of a subject is imaged with a CT scanner.

Imaging data may be collected after imaging a subject or portion of a subject. Such imaging data may be collected one time for any given subject. Alternatively, imaging data may be collected more than one time. For example, imaging data may be collected at a first time and at a second time that is later than the first time. Imaging data may also be collected more than two times, such as three of more times, for any given subject. When imaging data is collected more than one time for a subject, the time period between any collection of imaging data from a subject and any subsequent collection of imaging data from the subject may be immediately after the prior imaging or 30 minutes, 60 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more after the prior imaging, or any time period derivable therein. In some embodiments, the time period between a collection of imaging data from a subject and any subsequent collection of imaging data from the subject may be more than 24 hours, such as 1.5 days, 2 days, 5 days, 10 days, 15 days, 20 days, 25 days, 1 month, 3 months, 6 months, 9 months, 1 year, 2 years, 5 years, 10 years, 20 years, or more, or any range derivable therein. In certain aspects, imaging data collected for a subject at a first time may be compared with imaging data collected for the subject at a second time or at any time subsequent to the first time. For any methods disclosed herein that contemplate the collection of imaging data, the imaging data may be collected for a subject or for a portion of a subject.

In certain aspects, methods and compositions disclosed herein may be useful in planning a treatment program for a subject. For example, the treatment program may include radiation treatment. Thus, disclosed herein are methods that include planning a radiation treatment program for a subject based on imaging data collected with penetrating radiation after any of the compositions disclosed herein has been administered to the subject. For example, the subject may have one or more tumors in one or more tissues, and a method may include planning a radiation treatment protocol for treating the one or more tumors with radiation. The treatment may further comprise one or more additional therapies, such as a surgical therapy, a pharmacological therapy, an immunotherapy, chemotherapy, or gene therapy.

In some embodiments, a subject is treated while one views imaging data collected from the subject in substantially real-time as the imaging data is being collected. In certain aspects, data is collected and viewed in substantially real-time as a patient is receiving a treatment. Such data may be used to guide or inform the treatment in progress. For example, a subject may be treated with radiation wherein a portion of the subject is exposed to radiation, such as a portion of the subject having one or more tumors, and the radiation treatment is administered while imaging data is collected from the subject and viewed. In some aspects, changes in one or more tumors are assessed over time by comparing imaging data collected from a patient at different times. The imaging data may be collected by an imaging technique that uses penetrating radiation, and the imaging data may be collected after any of the compositions disclosed herein has been administered to the subject. Assessing changes in a tumor may comprise assessing changes in a tumor's size, morphology, or other characteristics visible using the particular imaging technique employed. In certain aspects, a subject is not treated while one views imaging data collected from the subject in substantially real-time as the imaging data is being collected—i.e., the imaging is independent of any treatment administered to the subject and may be exclusive of any treatment administered to the subject.

In certain embodiments, the subject is not receiving treatment for a disease, condition, or injury. In particular aspects, a subject is receiving treatment for a disease, condition, or injury, but the disclosed nanoparticles do not provide such treatment. For example, the nanoparticles may be used only to image a subject, and the nanoparticles may contain no group, moiety, molecule, or compound that treats a disease, condition, or injury of the subject. In some aspects, the disclosed nanoparticles neither provide a treatment nor enhance a treatment received by a subject. In some embodiments, the nanoparticles are administered to a subject for purposes of imaging the subject, but the nanoparticles provide no therapeutic benefit to the subject other than the benefits provided by imaging generally. Also provided are nanoparticles that do not provide radiation. In certain aspects, the nanoparticles contain no group, moiety, molecule, compound, or atom that provides radiation or is capable of providing radiation.

Also provided are imaging contrast agents. For example, an imaging contrast agent may comprise x-ray-opaque nanoparticles and a deoxyglucose or deoxyglucose derivative that is attached to the nanoparticles. In certain aspects, the deoxyglucose molecule that is attached to the nanoparticles is 2-Deoxy-D-Glucose. In additional embodiments the nanoparticle has PEG molecules attached to it. In further embodiments, the PEGylated nanoparticle has 2-Deoxy-D-Glucose molecules attached to the PEG molecules on the nanoparticle.

In some embodiments, methods of making an imaging contrast agent are provided. For instance, a method of making an imaging contrast may include the use of a linker molecule or linker group to attach one or more molecules, molecular groups, macromolecules, or compounds to a nanoparticle. One non-limiting example of a linker group is a mercapto group (or a thiol or —SH group). Thus, methods of making an imaging contrast agent are provided, wherein a plurality of mercapto groups in the 2-carbon position and a plurality of gold nanoparticles (AuNP) are subjected to a condensation reaction of 2-amino-deoxyglucose and mercaptosuccinic acid. Such methods of making an imaging contrast agent may include use of a solution comprising saline. For example, the solution comprising saline may be phosphate-buffered saline.

It is specifically contemplated that any limitation discussed with respect to one embodiment may apply to any other embodiment. Furthermore, any composition may be used in any method, and any method may be used to produce or to utilize any composition.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
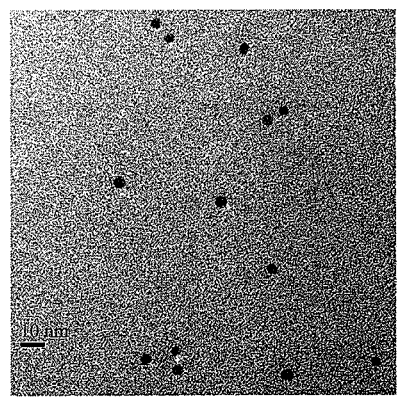
FIG. 1. TEM image of AuNP. The average particle size was measured to be 4.0±0.5 nm in diameter.

The present disclosure is based on the finding that certain nanoparticles are particularly useful as contrast agents for use in imaging, such as CT or X-ray imaging. Nanoparticles useful in the disclosed compositions and methods may include a chemical element, such as gold, and a tumor-targeting molecule, such as glucose or a glucose derivative.

Nanoparticles

Nanoparticles useful in the disclosed compositions and methods may comprise a chemical element, such as a metal. Non-limiting examples of metals useful in making nanoparticles include Fe, Cr, Al, Ga, In, Hf, Sn, Zr, Mo, Ti, V, Co, Ni, Cu, Y, Ta, W, Pb, B, Nb, Ge, Pr, U, Ce, Er, Nd, Mg, Ca, Ba, Sr, Au, Si, and combinations thereof.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In particular embodiments, the nanoparticle is spherical.

In one embodiment, a cross-sectional geometry of the particle may be one or more of circular, ellipsoidal, triangular, rectangular, or polygonal. A nanoparticle composition may consist essentially of spherical or non-spherical particles. Non-spherical nanoparticles may have the form of ellipsoids, which may have all three principal axes of differing lengths, or may be oblate or prelate ellipsoids of revolution. Non-spherical nanoparticles may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In some embodiments, a plurality of nanoparticles may consist essentially of spherical nanoparticles.

Synthesis

Nanoparticles may be synthesized by any method known in the art. For example, nanoparticles may be created by attrition or pyrolysis. In attrition, macro or micro scale particles are ground in a ball mill, a planetary ball mill, or other size reducing mechanism. The resulting particles are air classified to recover nanoparticles. In pyrolysis, a vaporous precursor (liquid or gas) is forced through an orifice at high pressure and burned. The resulting solid (a version of soot) is air classified to recover oxide particles from by-product gases. Pyrolysis often results in aggregates and agglomerates rather than singleton primary particles.

Gold nanoparticles (AuNP) may be synthesized using a citrate acid reduction method, such as reported in (Hayat, 1990; Hayat, 1991; Slot and Geuze, 1985), each of which is hereby incorporated by reference. Solvents useful in creating AuNPs include, but are not limited to deionized water, a saline-containing solution, or phosphate buffered saline (PBS).

Metal Coatings

In some embodiments, the nanoparticles are coated with a ligand, such as a chemical element, which may be, for example, a metal or metal oxide. Non-limiting examples of metals for use as ligands include Fe, Cr, Al, Ga, In, Hf, Sn, Zr, Mo, Ti, V, Co, Ni, Cu, Y, Ta, W, Pb, B, Nb, Ge, Pr, U, Ce, Er, Nd, Mg, Ca, Ba, Sr, Au, Si, and combinations thereof. Furthermore, metal-oxide-based materials are contemplated, including those based on silicon, germanium, tin, lead, antimony, bismuth, polonium, the lanthanides, and the actinides. Metal non-oxide nanoparticles include II-VI, III-V, and IV quantum dots; and metal oxide nanoparticles can include titanium oxide, zirconium oxide, aluminum oxide, iron oxide, tungsten oxide, cerium oxide, antimony oxide, and silicon oxide. Syntheses of metal oxides have been carried out using inorganic salts, such as salts of $Fe^{3+}$, $Cr^{3+}$, $A^{3+}$, $Ga^{3+}$, $In^{3+}$, $Hf^{4+}$, $Sn^{4+}$, $Zr^{4+}$, $Nb^{5+}$, $W^{6+}$, $Pr^{3+}$, $Er^{3+}$, $Nd^{3+}$, $Ce^{3+}$, $U^{3+}$, $Y^{3+}$, and combinations thereof.

In some embodiments, a metal coating is deposited on the surface of the nanoparticle. The metal coating may be deposited using any method known to those of ordinary skill in the art. Non-limiting examples of such techniques include chemical vapor deposition, ion implantation, spray painting, and the like. Metal coatings may be fabricated by placing nanoparticles in a composition comprising a metal (or metal salt) and a solvent (or mixture of solvents). A solvent capable of dissolving or dispersing the metal salt differs depending on the functional groups of the solvent. The solvent may include water, ketones such as acetone and methyl ethyl ketone, esters such as ethyl acetate, alcohols such as methanol and ethanol, aprotic polar solvents such as dimethylformamide, dimethyl sulfoxide, sulfolane, diglyme and hexamethylphosphorotriamide, and, further, nitromethane and acetonitrile, among others. Water and hydrophilic organic solvents, such as alcohols or ketones, in admixture with water can be suitably used. The concentration of the metal salt may vary depending on the solvent used for dissolving the salt but may be in an amount from about 0.001% to the saturated solution concentration for the salt.

Other Ligands

Some embodiments concern nanoparticles with one or more attached ligands other than metals. A ligand may be an ion, a molecule, a compound, a macromolecule, or a molecular group. Examples of ligands include organic molecules and drugs. Biodegradable, biopolymer (e.g., polypeptides such as BSA, polysaccharides, etc.), other biological materials (e.g., carbohydrates), and/or polymeric compounds are contemplated as possible ligands. Gold is also contemplated as a ligand due to its well-known reactivity profiles and biological inertness.

The nanoparticles set forth herein may be coated with a ligand that is selected from the group consisting of dextran, dendrimers, amphiphilic polymers/bio-polymers (e.g., phospholipids and peptides), polymers, surfactants or chemical compounds. In particular embodiments, the nanoparticles are attached to glucose or a glucose derivative. Glucose is a simple sugar having the formula $C_6H_{12}O_6$. The glucose molecule may be D-glucose or L-glucose. The glucose derivative may be deoxyglucose, 2-Deoxy-D-Glucose, alpha-D-glucopyranose, beta-D-glucopyranose, 3-phospho-D-glycerate, alpha-D-glucose-1-phosphate, alpha-D-glucose-6-phosphate, beta-D-glucose-6-phosphate, beta-D-glucuronate, beta-D-glucosamine, beta-D-glucosamine-6-phosphate, D-glucosamine-6-phosphate, D-glucosamine, D-glucosaminide, D-glucosaminyl-D-glucosaminide, glucose-1,6-bisphosphate, glucose-1-phosphate, glucose-6-phosphate, or others known to those in the art. The glucose or glucose derivative may be attached to the nanoparticle at any suitable position in the glucose or glucose derivative molecule, such as at the 1-carbon position, 2-carbon position, 3-carbon position, and so forth. In particular embodiments, the glucose derivative is deoxyglucose or 2-Deoxy-D-Glucose. In certain aspects, the 2-Deoxy-D-Glucose is attached to the nanoparticle at the 2-carbon site on the 2-Deoxy-D-Glucose.

Surface Modification and Linkers

Nanoparticles useful in methods and compositions disclosed herein may be subjected to surface modification so that a ligand can readily bind to the surface thereof. The surface modification of the nanoparticles can be accomplished, for example, by treating the nanoparticle solution with a coupling agent (linker)-containing solution. For example, the coupling agent may be a silane coupling agent.

Exemplary functional groups of linkers include, but are not limited to, the following: a hydroxyl, a carboxyl, an amino, a phosphate, a phosphonate, a sulfate, a sulfite, a sulfenate, a sulfonate, a sulfonate, a sulfoxide, a sulfone, an amide, an ester, a ketone, an aldehyde, a nitrile, an alkene, an alkyne, an ether, a thiol (or mercapto), a hydroxyamic acid, a silane, a silicate, a carbamodithionate, a dithionate, a mercaptan, a disulfide, a peroxide and a nitronate group.

The linker can be used in the form of a diluted solution prepared by using such a solvent as mentioned above and is generally used in the form of an aqueous solution. As for the linker concentration, any appropriate concentration can be used and, for example, a linker solution having a concentration of 0.001 to 5.0%, or 0.01 to 1.0%, may be added to the solution.

While numerous types of linkers are known that can successfully be employed to conjugate moieties, certain linkers will generally be preferred over other linkers, based on differing pharmacologic characteristics and capabilities. In particular embodiments, the linker is a thiol (or mercapto or —SH) group that is used to link molecules to gold nanoparticles.

Other preferred linkers include, but are not limited to, polyethylene glycol, a dendrimer, a molecule comprising a tert-butyl protecting group, a molecule comprising an isobutylene oxide connection, an amino benzyl alcohol, a hydroxy benzyl alcohol connection, an aminobenzene dimethanol, an aminobenzene trimethanol, a hydroxybenzene dimethanol, a hydroxybenzene trimethanol, a vinyl sulfoxide, a substituted vinyl sulfoxide, a substituted methoxymethyl connection, a substituted vinyl ether connection, a carbonate connection, an ester connection, an anhydride connection, a substituted carbamic anhydride connection, a carbonic anhydride connection, a substituted urea connection, a substituted urethane connection, a substituted guanidine connection, an ether connection, a mercaptan connection, a sulfoxide connection, a sulfinate connection, a sulfonate connection, a sulfenate connection, a nitronate connection, a sulfite connection, a sulfate connection, a phosphate connection, a phosphonate connection, a phosphine connection, a silane connection, a silicate connection, a disulfide connection, a peroxide connection, an alkane connection, an alkene connection, an alkyne connection, an iodonium connection, an amino connection, a substituted allyl ether connection, a substituted benzyl ether connection and an imine connection.

In some embodiments, the linker is further defined as a cross-linking reagent. Cross-linking reagents are used to form molecular bridges that tie together functional groups of two different molecules.

Biocompatible Polymers

In some aspects, nanoparticles are attached to a biocompatible polymer to improve the in vivo half-life of the particle. The biocompatible polymer may be a hydrophilic polymer, such as polyethylene glycol (PEG), polyoxyethylene, polymethylene glycol, polytrimethylene glycols, polyvinyl-pyrrolidones, and derivatives thereof.

In certain embodiments, the biocompatible polymer is PEG or a derivative thereof, such as monomethoxypolyethylene glycol (mPEG) or mPEG-succinate-N-hydroxysuccinimide ester (SS-PEG). PEG is also known as polyethylene oxide (PEO) or polyoxyethylene (POE). The PEG may have an average molecular weight over a range of from about 100 to about 20,000 Daltons, or about 1000 to 20,000 Daltons. In some aspects, PEG molecules may be mono-, di-, or multifunctional polyethylene glycols PEGs. Monofunctional PEG has only one reactive hydroxy group, while difunctional PEG has reactive groups at each end. Monofunctional PEG may have an average molecular weight between about 100 and about 15,000 Daltons, or between about 200 and about 8,000 Daltons. Difunctional PEG may have an average molecular weight of about 400 to about 40,000, or about 3,000 to about 10,000 Daltons. Multifunctional PEG have an average molecular weight between about 3,000 and 100,000 Daltons.

Those of ordinary skill in the art will appreciate that synthetic polymers such as polyethylene glycol cannot be prepared practically to have exact molecular weights, and that the term "molecular weight" as used herein refers to the average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weight indicates that the average molecular weight may be any value between the limits specified, and may include molecules outside those limits. Thus, a molecular weight range of about 800 to about 20,000 Daltons indicates an average molecular weight of at least about 800 Daltons, ranging up to about 20 kDa.

Solutions

When in solution in a composition, the nanoparticles may generally be present in the solution in an amount of about 0.0000001 wt % to about 100 wt % (solid-free powder), based on the total weight of the solution. In one embodiment, the nanoparticles may generally be present in the solution in an amount of about 0.000001 wt % to about 15 wt %. In another embodiment, the nanoparticles may generally be present in the solution in an amount of about 0.01 wt % to about 1 wt %. In yet another embodiment, the nanoparticles may generally be present in the solution in an amount of about 1 wt % to about 10 wt %. Such solutions may be administered to a subject.

Other Modifications

In some embodiments, the nanoparticles can be functionalized with molecules to provide a positive or negative charge. Alternatively, the nanoparticles can be functionalized with molecules to provide a hydrophobic or hydrophilic surface.

Imaging Techniques

In some aspects, nanoparticles are useful for imaging subjects, which may include organisms, cells, tissues, organs, biological samples, and the like. Such imaging may be performed by any method known in the art. For example, useful imaging methods include, but are not limited to, magnetic resonance imaging (MRI), optical imaging, optical coherence tomography, X-ray, computed tomography (CT), positron emission tomography (PET), single photon emission computed tomography (SPECT), or combinations thereof.

Imaging techniques using nanoparticles disclosed herein can be performed one time on a subject (or portion of a subject), or can be performed multiple times on a subject (or portion of a subject) over time. For example, multiple images may be acquired over time to observe changes in a subject or portion of a subject, such as changes associated with the progression, maintenance, or treatment of a disease, condition, or injury.

CT Imaging

In particular aspects, nanoparticles are useful in methods involving computed tomography (CT) imaging, which is a medical imaging method that employs tomography created by computer processing. Digital geometry processing is used to generate a three-dimensional image of the inside of an object from a large series of two-dimensional X-ray images taken around a single axis of rotation. This process provides a volume of data that can be manipulated to demonstrate various bodily structures based on their ability to block the X-ray beam. Modern scanners allow the data to be reformatted in various planes or even as volumetric (3D) representations of structures. Although most common in medicine, CT is also used in other fields, such as nondestructive materials testing.

The data stream representing the varying radiographic intensity sensed at the different detectors in the CT scanner is computer processed to calculate cross-sectional estimations of the radiographic density, which is expressed in Hounsfield units (HU).

Subjects

A subject to be imaged may be an organism, such as a mammal (e.g., human). In some aspects, a portion of a subject of a subject is imaged, such as a biological sample or biological material. A subject, such as a mammal or a human, may have a disease, condition, or injury. In some embodiments, the subject has or is at risk of developing a neoplastic disease, such as cancer. The cancer can be any type of cancer. For example, the cancer may be melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, or bladder.

In certain aspects, the methods and compositions disclosed herein are useful in imaging one or more tumors in a subject or biological sample. Non-limiting examples of tumors that may be imaged using the disclosed methods and compositions include tumors of the brain (glioblastomas, medulloblastoma, astrocytoma, oligodendroglioma, ependymomas), lung, liver, spleen, kidney, lymph node, small intestine, pancreas, blood cells, colon, stomach, breast, endometrium, prostate, testicle, ovary, skin, head and neck, esophagus, bone marrow, blood and other tissue.

The subject can be a subject who is known or suspected of being free of a particular disease or health-related condition. The subject, for example, can be a subject with no known disease or health-related condition (i.e., a healthy subject). In some embodiments, the subject is a subject at risk of developing a particular disease or health-related condition. For example, the subject may have a history of cancer that has been treated in the past, who is at risk of developing a recurrence of the cancer. The subject may be a subject at risk of developing a recurrent cancer because of a genetic predisposition or as a result of past chemotherapy. Alternatively, the subject may be a subject with a history of successfully treated cancer who is currently disease-free, but who is at risk of developing a second primary tumor. For example, the risk may be the result of past radiation therapy or chemotherapy that was applied as treatment of a first primary tumor. In some embodiments, the subject may be a subject with a first disease or health-related condition, who is at risk of development of a second disease or health-related condition.

As used herein, "treatment" and "treating" refer to administration or application of an agent, drug, or remedy to a subject or performance of a procedure or modality on a subject for the purpose of obtaining a therapeutic benefit of a disease or health-related condition. A disease, condition, health-related condition, or injury can be any pathological condition of a body part, an organ, or a system resulting from any cause, such as infection, genetic defect, trauma, and/or environmental stress. The cause may or may not be known. Examples of such conditions include, but are not limited to, premalignant states, dysplasias, cancer, and other hyperproliferative diseases.

Pharmaceutical Preparations

Certain of the methods and compositions set forth herein pertain to the administration of nanoparticles to a subject, such as a mammal. In such applications, the nanoparticles should be in a pharmaceutically acceptable formulation.

Compositions

As used herein, a "pharmaceutically acceptable formulation" may include any of a number of carriers such as solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient (e.g., nanoparticles described herein), its use in pharmaceutical compositions is contemplated. A composition may comprise different types of carriers depending on whether it is to be administered in solid, liquid or aerosol form, and whether it need be sterile for such routes of administration as injection.

Supplementary active ingredients can also be incorporated into the compositions. For human administration, preparations should meet sterility, pyrogenicity, general safety and purity standards as required by FDA Office of Biologics standards. Administration may be by any known route.

Also contemplated are methods using compositions that are sterile solutions for injection or for application by any other route. A person of ordinary skill in the art would be familiar with techniques for generating sterile solutions for injection or application by any other route. Sterile injectable solutions are prepared by incorporating the active compounds in the required amount in an appropriate solvent with various other ingredients familiar to a person of skill in the art.

The formulation of the composition may vary depending upon the route of administration. For parenteral administration in an aqueous solution, for example, the solution should be suitably buffered if necessary and the liquid diluent first rendered isotonic with sufficient saline or glucose. Sterile aqueous media which can be employed will be known to those of skill in the art in light of the present disclosure.

In certain embodiments, a pharmaceutical composition includes at least about 10, 20, 30, 40, 50, 60, 70, 80, 90, 100, 200, 300, 400, 500, or more mg/mL of nanoparticles disclosed herein.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, one may use nasal solutions or sprays, aerosols or inhalants. Nasal solutions are usually aqueous solutions designed to be administered to the nasal passages in drops or sprays.

Solid compositions for oral administration are also contemplated. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects, the oral composition may be prepared as a syrup or elixir. Additional formulations which are suitable for other modes of administration include suppositories. Suppositories are solid dosage forms of various weights and shapes for insertion into the rectum, vagina or urethra.

Sterile injectable solutions are prepared by incorporating the active compounds (e.g., nanoparticles) in the required amount in the appropriate solvent with various of the other ingredients enumerated above. The liquid medium should be suitably buffered if necessary and the liquid diluent first rendered isotonic prior to injection with sufficient saline or glucose.

Routes of Administration

Upon formulation, solutions will be administered in a manner compatible with the dosage formulation and in such amount as is effective. For example, nanoparticles may be administered in such an amount as is effective for the particular imaging application desired.

The composition can be administered to the subject using any method known to those of ordinary skill in the art. The mode of administration may vary based on the application. For example, the mode of administration may vary depending on the particular cell, tissue, organ, portion of the body, or subject to be imaged. For example, the composition may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering nanoparticles to a subject.

Dosage

An effective amount of a nanoparticle composition is determined based on the intended goal, for example, based on the imaging method and the subject or portion of a subject to be imaged. The quantity to be administered may also vary based on the particular route of administration to be used.

A pharmaceutical composition to be administered to a subject may include at least about 10, 20, 30, 40, 50, 60, 70, 80, 90, 100, 200, 300, 400, 500, or more mg/mL of nanoparticles disclosed herein. In some embodiments, the composition is administered at a concentration of about 60 mg/mL of nanoparticles. In other embodiments, the composition is administered at a concentration of about 100 mg/mL. In some aspects, the composition may be administered at a dosage of at least 0.1, 0.2, 0.3, 0.4, 0.5, 0.6, 0.7, 0.8, 0.9, 1.0, 2.0, 3.0 or more mL of a 60 mg/mL solution per 500 grams weight of a subject. In some embodiments, the composition may be administered at a dosage of at least 0.1, 0.2, 0.3, 0.4, 0.5, 0.6, 0.7, 0.8, 0.9, 1.0, 2.0, 3.0 mL of a 100 mg/mL solution per 500 grams weight of a subject. In some aspects, at least about 10, 20, 30, 40, 50, 60, 70, 80, 90, 100 or more mg of nanoparticles are administered. In other aspects, at least about 0.3, 0.4, 0.5, 0.6, 0.7, 0.8, 0.9, 1.0, 1.2, 1.3, 1.4, 1.5, 1.6, 1.7, 1.8, 1.9, 2.0, 2.5, 3.0, or more grams of nanoparticles are administered. In some embodiments regarding a small animal, such as a mouse or a rat, a dosage of 5-70 mg of the nanoparticles may be administered, depending on the size of the subject. In some embodiments regarding a large animal, such as a human, a dosage of 0.5-2.0 gram of nanoparticles may be administered, depending on the size of the subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art.

Kits

Certain embodiments are generally concerned with kits that include nanoparticle compositions and other compositions disclosed herein. For example, in some embodiments, the kit includes one or more sealed containers that contain a predetermined quantity of nanoparticle.

A kit may include a sealed vial containing a predetermined quantity of nanoparticles. In further embodiments, the nanoparticles consist of or are coated with a metal or other ligand as discussed above.

EXAMPLES

The following examples are included to demonstrate preferred embodiments. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In Vitro Uptake of AuNP-DG

Colloidal AuNP was synthesized using a citrate acid reduction method similar to that reported previously (Hayat, 1991; Slot and Geuze, 1985). The AuNP suspension was repeatedly centrifuged until it reached a concentration of 60 mg Au/mL. The solvent of the final product was changed from deionized water to phosphate buffered saline (PBS, pH 7.4). The prepared AuNPs were observed to be a dark-red-colored aqueous suspension with a mean particle size of 4 nm in diameter as determined using Transmission Electron Microscopy (TEM, FEI Tecnai™ F30, FEI Co., USA). FIG. 1 shows a TEM picture of the unlabeled gold nanoparticles.

The conjugation of 1 or 2-DG with the AuNP core was accomplished by placing a mercapto group in the 1- or 2-carbon position, respectively, via condensation reaction of 2-amino-deoxyglucose with mercaptosuccinic acid (Hermanson, 2008). The reaction solution was prepared by dissolving mercaptosuccinic acid ($8 \times 10^{-2}$ M), D-(+)-Glucosamine hydrochloride ($8 \times 10^{-1}$ M), 1-ethyl-3-(3-dimethylaminopropyl)-Carbodiimide) (EDC, $4 \times 10^{-2}$ M) and N-hydroxysuccinimide (NHS, $4 \times 10^{-2}$ M) in deionized water. This solution was kept at room temperature for two hours and then added to the concentrated AuNP suspension of equal volume. All chemicals were purchased from a commercial supplier (Sigma-Aldrich Co., USA).

The overall size of the AuNP-DG was estimated to be slightly larger than that of the unlabeled AuNP. Due to the lack of an effective staining technique for the visualization of the 2-DG molecules, TEM images of the AuNP-DG were not acquired.

As an example of the contrast-producing property of the gold nanoparticles, an AuNP sample at a concentration of 30 mg Au/mL was imaged using a microCT scanner (TRIUMPH™ X-O™ CT System, Gamma Medica-Ideas Inc., USA). A vial of water was also included in the CT scan to serve as the reference. The images were acquired at 75 kVp, 135 µA with an 1148×1120 matrix size and 360 views, averaging 5 frames per view. The dataset was reconstructed into a 512×512×512 image volume. Image reconstruction was performed using a general-purpose filtered back projection algorithm, implemented by the reconstruction software supplied with the imaging system. The reconstructed image data were transferred to a remote computer for further analysis.

Figure 2:
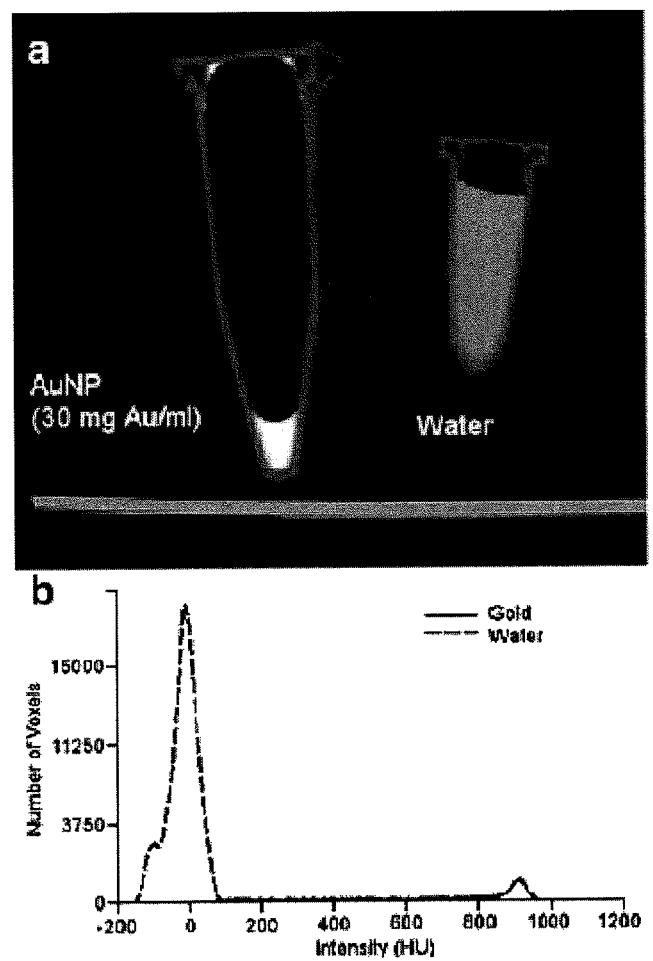
FIGS. 2A, 2B. A. A coronal slice from microCT scans of AuNP (30 mg Au/ml) and water. The contrast between the AuNP and the water is clearly seen. B. Histogram of voxel intensity expressed in Hounsfield units (HU) for the water and AuNP samples in FIG. 2A.

The reconstructed image data were analyzed using a commercial image processing software package (AMIRA™ 5.2, Visage Imaging Inc., USA). To assess the contrast enhancement, the CT signal intensity was expressed in Hounsfield Units (HU) (Ambroseand and Hounsfield, 1973). To make this conversion, a two-point calibration method was used. In this method, the CT signal intensity in the water volume was set to 0 HU, and the CT signal intensity in the air volume was set to −1000 HU. The HU values of other materials were then obtained by linear extrapolation. FIG. 2A shows one coronal image from these MicroCT scans. The contrast enhancement in the AuNP sample is clearly seen in this picture. The measured CT intensity of the AuNP sample is 900±50 HU, consistent with observations by others (Kim et al., 2007). Voxel intensity histograms for both the water sample and the AuNP sample are shown in FIG. 2B. Statistical analysis was performed using the statistical analysis software G*Power (version 3.0.10. Heinrich-Heine University, Germany).

The human alveolar epithelial cancer cell line A-549 was used to test in vitro cellular uptake of the AuNP-DG (Su et al., 2006). Prior to the imaging experiments, trypan blue staining was performed on the A-549 cells after incubation with varying concentrations of AuNP-DG suspended in PBS and DMEM media in order to assess cell membrane integrity as a marker for cell viability. The data acquired were used to identify non-toxic levels of AuNP-DG in the growth media that would not disrupt the cell membrane but still provide a suitable contrast level.

Figure 3:
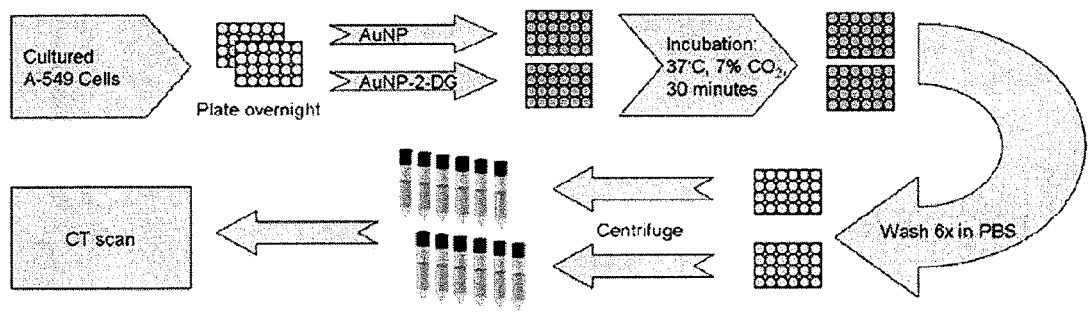
FIG. 3. Cell preparation flow chart.

Approximately $1 \times 10^5$ A-549 cells, maintained in DMEM media supplemented with 10% fetal bovine serum (FBS) and 1% penicillin-streptomycin at 37° C. in 7% $CO_2$, were plated in 24-well cell culture plates 24 hours prior to the experiment. Two groups of cell samples were prepared, each containing 4 wells. Twenty-four hours after plating, the A-549 cells were treated with AuNP and AuNP-DG, respectively, for 30 minutes (at 37° C., 7% $CO_2$). Following the incubation, the cells were washed with sterile PBS six times to remove excess gold nanoparticles. The cells were then transferred to plastic vials containing fresh growth media and spun to cell pellets using a centrifuge. The cell pellets were approximately 2 mm in diameter and adhered to the bottom of the vials in a half-moon shape. FIG. 3 provides a flow diagram detailing the cell preparation process.

The cell samples were imaged using a MicroCT scanner (Triumph™ X-O™, Gamma Medica-Ideas Inc., USA) immediately after centrifugation. For data acquisition, the vials containing the cell pellets were stacked horizontally with their long axes parallel to the axis of rotation (z-axis) of the imaging system. The images were acquired at 75 kVp, 135 µA with a 512×512 matrix size and 360 views over a full circle. Image reconstruction was performed using a proprietary filtered back projection algorithm implemented in the imaging system's on-board reconstruction software (Cobra, Exxim Computing Corporation, USA). The reconstructed image volume consisted of 512×512×512 volume elements with an isotropic size of <60 µm. The reconstructed image data were transferred to an off-line computer for further analysis.

Figure 4:
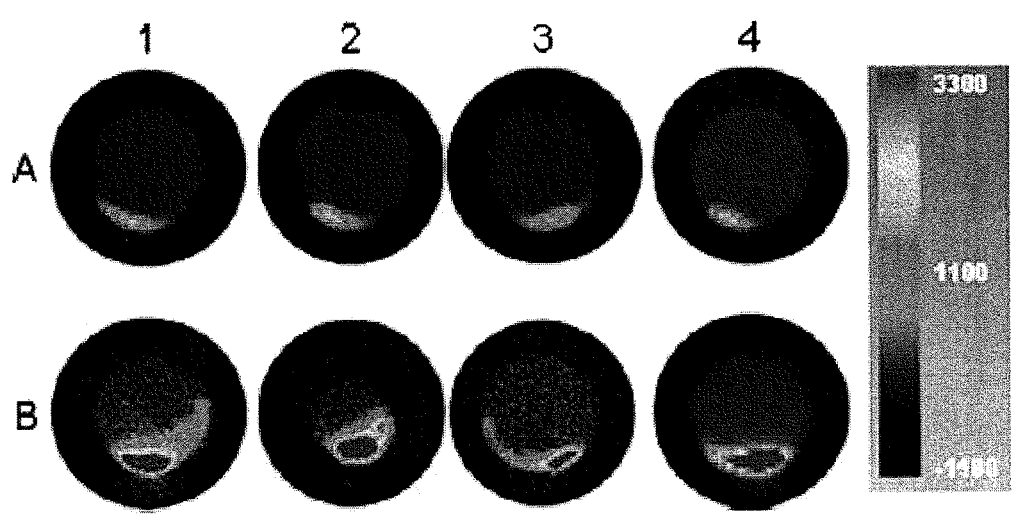
FIG. 4A, 4B. Axial CT slices of two groups of cell samples. A. Cells incubated with AuNP. B. Cells incubated with AuNP-DG. Intensity is expressed in Hounsfield units (HU) with shading shown in the legend on the right. Because the cell pellets span more than one slice, only one representative slice from each cell sample is shown. The contrast enhancement in group-B is apparent. Trypan blue staining (not shown) was performed on cell samples after imaging in order to assess cell membrane integrity as a marker for cell viability.
Figure 5:
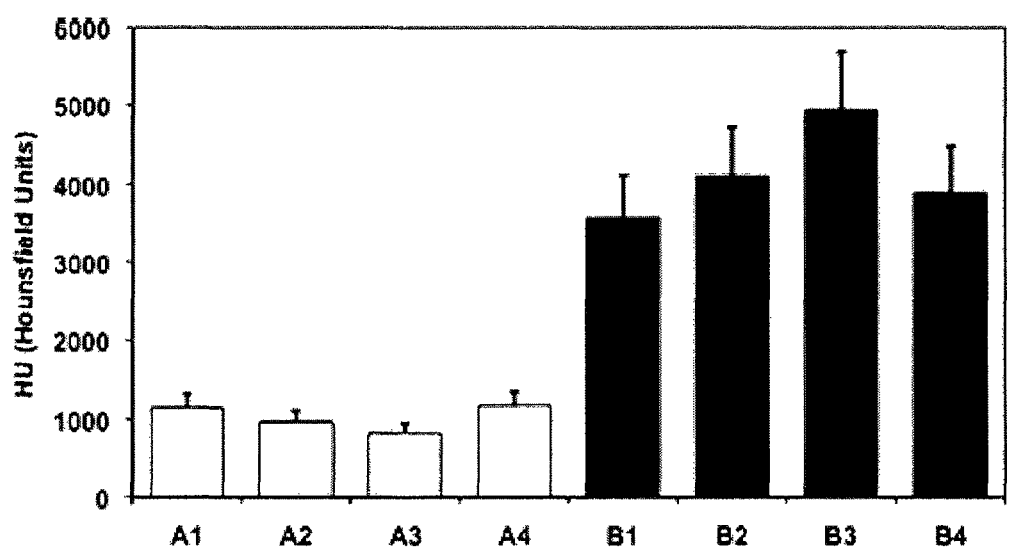
FIG. 5. CT contrast values (HU) of A-549 cancer cell samples incubated with AuNP (A1 to A4) and those incubated with AuNP-DG (B1 to B4).
Figure 6:
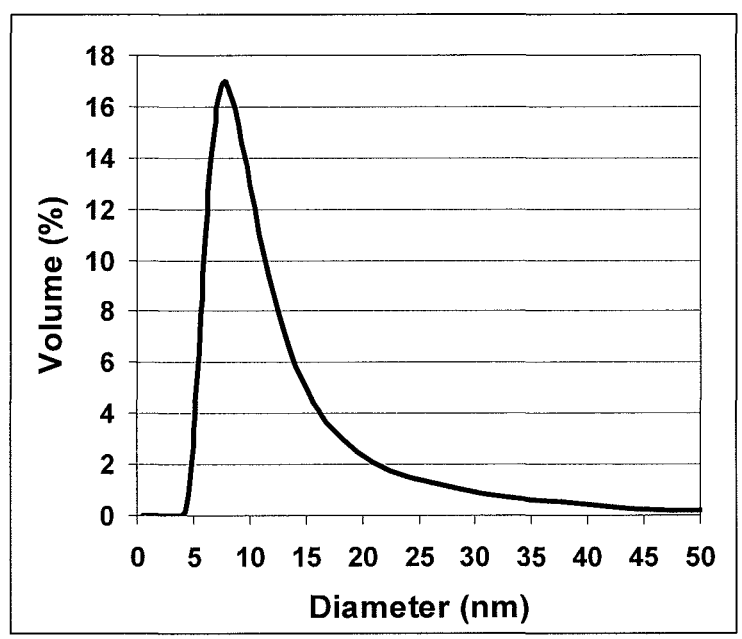
FIG. 6. Dynamic light scattering measurement showing the distribution of the hydrodynamic diameter of the AuNP-2-DG. The mean hydrodynamic diameter is approximately 8 nm.

FIG. 4 shows axial CT slices of the cell samples incubated with AuNP (Group A, FIG. 4A) or incubated with AuNP-DG (Group B, FIG. 4B). The intensity is expressed in Hounsfield Units (HU) as previously described. Because the cell pellets span more than one slice, only one representative slice is shown for each cell sample. In these images, the contrast enhancement in Group B over that in Group A is apparent. CT contrast values (HU) were measured in the center of the cell pellets presented in FIG. 4. The CT values are shown in FIG. 5. The CT contrast in the cells incubated with the AuNP-DG is on average more than 3 times higher than that of the cells incubated with the unlabeled AuNP.

The CT contrast is directly proportional to the amount of the contrast agent taken up by the cells. Therefore, the higher contrast enhancement in the Group B samples strongly suggests enhanced uptake of the 2-DG labeled gold nanoparticles over the unlabeled gold nanoparticles by the A-549 cells. Both Group A and Group B exhibit much higher CT contrast with respect to typical soft tissue, which has a CT contrast ranging from 0 to 50 HU). The enhanced contrast in the AuNP-incubated cell samples is likely due to insufficient wash-out or permeation of the AuNP through the cell membrane. Based on cell viability assays, cell membranes appeared to be intact in a majority of the cells incubated with AuNP-DG.

Figure 7:
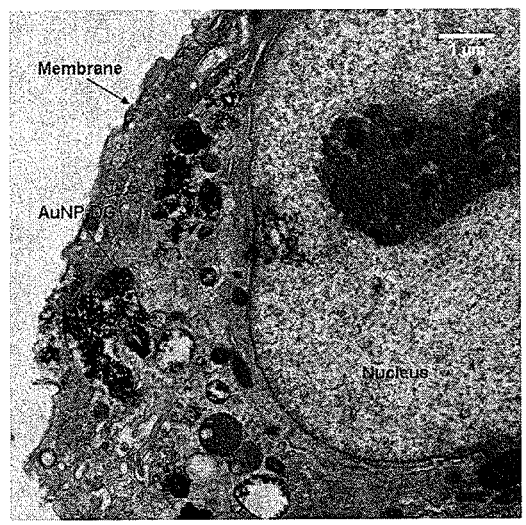
FIG. 7. TEM image showing internalization of the AuNP-2-DG by an A-549 cancer cell.

TEM images showed internalization of AuNP-2-DG by the A-549 cancer cells (FIG. 7). As is seen in FIG. 7, the gold nanoparticles are clearly seen inside the cell, along with the cell nucleus. Unlabeled AuNP suspended in PBS and cells incubated with AuNP-2-DG were imaged using a Transmission Electron Microscope (TEM, FEI Tecnai™ F30, FEI Co., USA) at 300 keV electron energy. For TEM imaging, cells were fixed using the HPF technique (Koster and Klumperman, 2003) in which the cell samples were frozen with liquid nitrogen at 77 K under 700 bar pressure (BAL-TEC HPM 010 HPF Machine, ABRA Fluid AG, Switzerland). The freezing time was 7 ms. The frozen cells were then sectioned into 100 nm thick slices using a diamond sectioning knife (Leica, Germany) and stained using osmium tetroxide at a concentration of 2% in acetone followed by uranyl acetate and lead citrate (Hayat, 2000). This technique captures the cells in a 'live' state and avoids detrimental artifacts such as the formation of crystalline ice.

Figure 8:
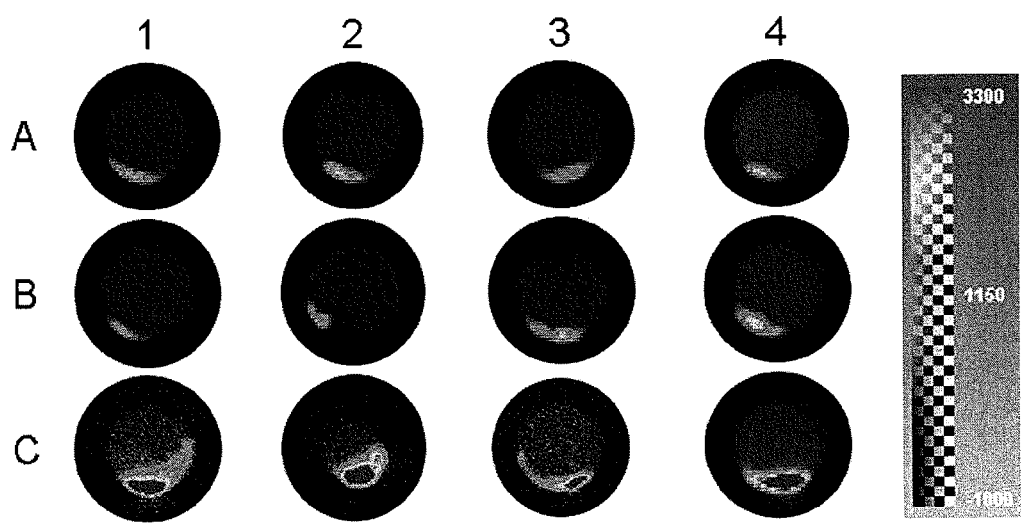
FIG. 8A, 8B, 8C. Transaxial CT slices of three groups of cell samples. A. Cells incubated with AuNP. B. Cells incubated with AuNP-1-DG. C. Cell incubated with AuNP-2-DG. The intensity is expressed in Hounsfield Units (HU). The contrast enhancement in Group-C is apparent.

FIG. 8 compares uptake of AuNP, AuNP-1-DG, and AuNP-2-DG. A-549 cells were planted in DMEM media supplemented with 10% fetal bovine serum (FBS) and 1% penicillin-streptomycin at 37° C. in 7% $CO_2$ using 24-well cell culture plates, 24 hours prior to the experiment. Each well contained approximately 100,000 cells. Three groups of cell samples were prepared each containing 4 wells. After the 24-hour anchoring period, the cells in Group-A, Group-B and Group-C were incubated (37° C., 7% $CO_2$, 100 µL DMEM, 100 µL of gold nanoparticle suspended in sterile PBS at 60 mg Au/mL concentration) with AuNP, AuNP-1-DG and AuNP-2-DG, respectively, for 30 minutes. Following the incubation, the cells were washed with cold PBS for six times to remove the excess gold nanoparticles. The cells were then transferred to plastic vials containing fresh growth media and spun to cell pellets using a centrifuge. The cell pellets were approximately 2 mm in diameter and adhered to the bottom of the vials in a half-moon shape.

FIG. 8 shows axial CT slices of the cell samples in Group-A (incubated with AuNP, FIG. 8A), Group-B (incubated with AuNP-1-DG, FIG. 8B) and Group-C (incubated with AuNP-2-DG, FIG. 8C). The intensity is expressed in Hounsfield Units (HU) as described above. Several slices of the CT volume intersected with the cell pellets. A representative slice with highest CT contrast of each sample is shown. In these slices, the contrast enhancement in Group-C is apparent.

Figure 9:
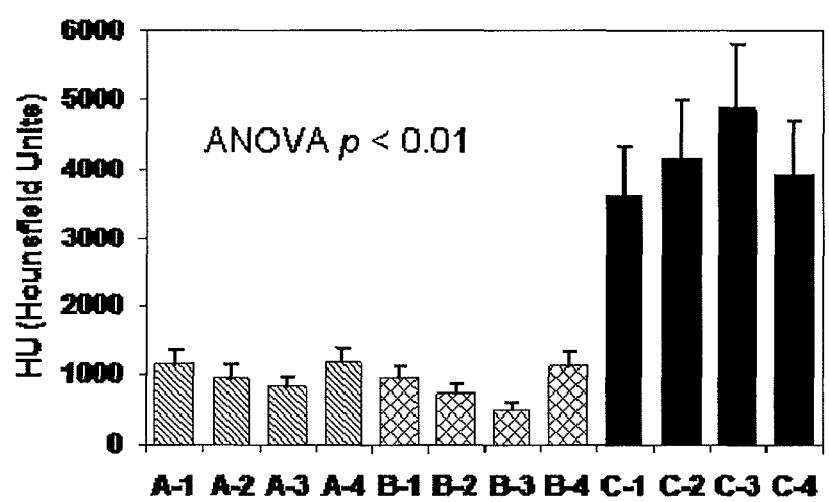
FIG. 9. CT intensity (HU) measured in the center of the cell pellets shown in FIG. 8.

The CT contrast values (HU), measured in the center of the cell pellets, as presented in FIG. 8, are shown in FIG. 9. As shown in FIG. 9, the CT contrast in the cells incubated with the AuNP-2-DG is on average more than 3 times higher than that of the cells incubated with either the unlabeled AuNP or the AuNP-1-DG. An ANOVA analysis based on the HU values resulted in a p-value of <0.01 for rejecting the null hypothesis (no difference in HU between the three groups). Further Bonferroni-corrected t-tests showed that the t-values between the three groups, $t_{AuNP:AuNP-1-DG}$, $t_{AuNP:AuNP-2-DG}$ and $t_{AuNP-1-DG:AuNP-2-DG}$, are −0.262 (p~1.00), 4.086 (p<0.02) and 4.349 (p<0.02), respectively.

These studies demonstrate the usefulness of AuNP conjugated to 2-DG as a metabolic functional contrast agent, which is particularly useful for CT imaging. The contrast agent possessed the ability to specifically target tumor cells. The functional CT techniques disclosed here provide high-resolution anatomical and functional images in a single CT scan.

Example 2

In Vivo Uptake of AuNP-DG

Figure 10:
FIG. 10. Mouse 8 hours post-injection. The tumor appears black, indicating the uptake of AuNP-DG in the tumor and liver.

To assess in vivo uptake of AuNP-DG, gold nanoparticles were suspended in sterile PBS at 60 mg Au/mL. The viscosity of this suspension is low enough that it can pass through the syringe without difficulty. The mice were interstitially injected with a 20 nanometer (nm) gold nanoparticle suspension in sterile PBS in and around the tumors. For each animal, five injections were given round the tumor, each with 10 mL of gold nanoparticle suspension at a concentration of 60 mg Au/mL. FIG. 10 shows a mouse at 8 hours post-injection. The tumor appears black indicating the uptake of AuNP-DG in the tumor. Liver uptake was also observed after 4 hours. Although not wishing to be bound by any theory, uptake in the liver may indicate that the nanoparticles triggered the immune system and were cleared by the macrophages.

Figure 11A:
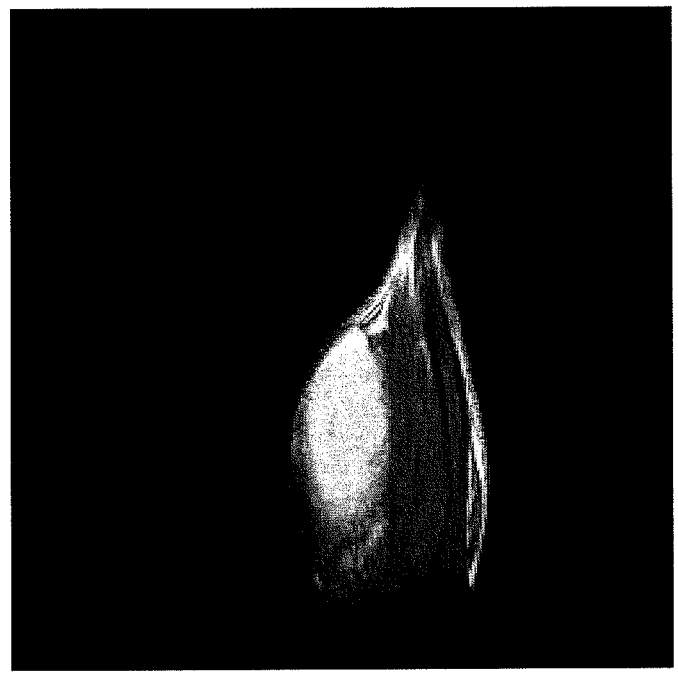
FIGS. 11A, 11B. Tumor images. A. MRI image of tumor pictured in FIG. 10. B. Axial CT slice of showing tumor pictured in FIG. 10 before (left) and after (right) injection of AuNP-DG.
Figure 11B:
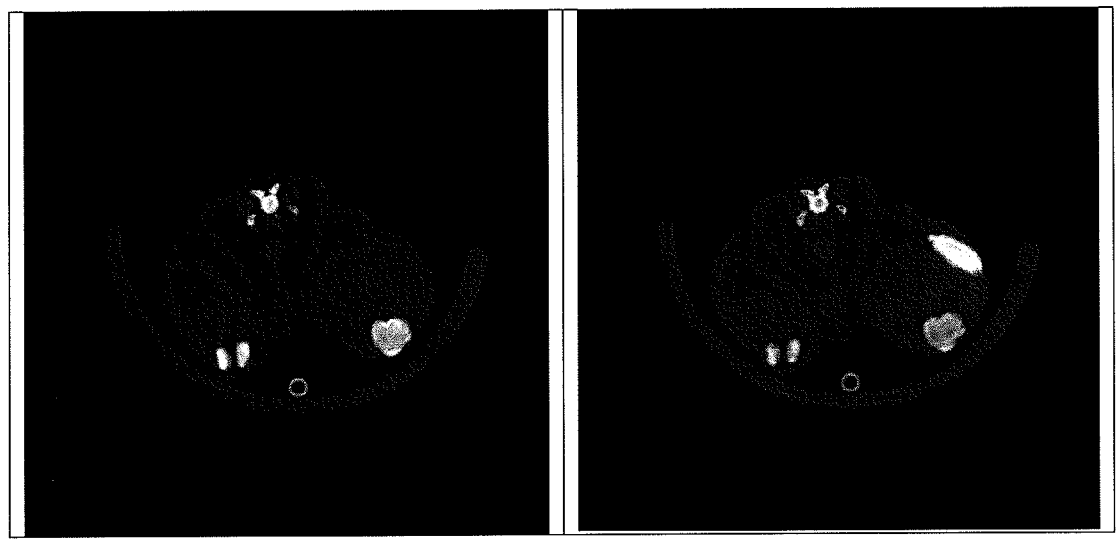

MRI images of the tumor pictured in FIG. 10 are shown in FIG. 11A and FIG. 11B. FIG. 11B provides axial CT slices of the tumor before (left, FIG. 11B) and after (right, FIG. 11B) injection of AuNP-DG. The MRI imaging was performed with a special small animal coil. The sagittal slice as shown was acquired with TR=4000 ms, TE=27.5 ms with one echo and 25 slices. The field of view (FOV) is 2.56 cm with an array size of 256×256. The choice of this sequence was made to emphasize the tumor. The extent of the tumor can be seen clearly in the MR images (FIG. 11A). The same mice were then were interstitially injected with the 20 nanometer (nm) gold AuNP-DG suspension in sterile PBS in and around the tumors. For each animal five injections were given spread around the tumor, each with 10 mL of gold nanoparticle suspension at a concentration of 60 mg Au/mL. Images were obtained using Micro CT by Flex Triumph, Gamma Medica IDEAS, USA at different time points (FIG. 11B). The imaging technique used in this study involved 75 kVp, 360 projections, and average 5 frames per projection. Images were reconstructed into 512×512×512 volume using generic filtered back projection. These images demonstrate the usefulness of nanoparticles disclosed herein for microCT imaging of a tumor.

Figure 12:
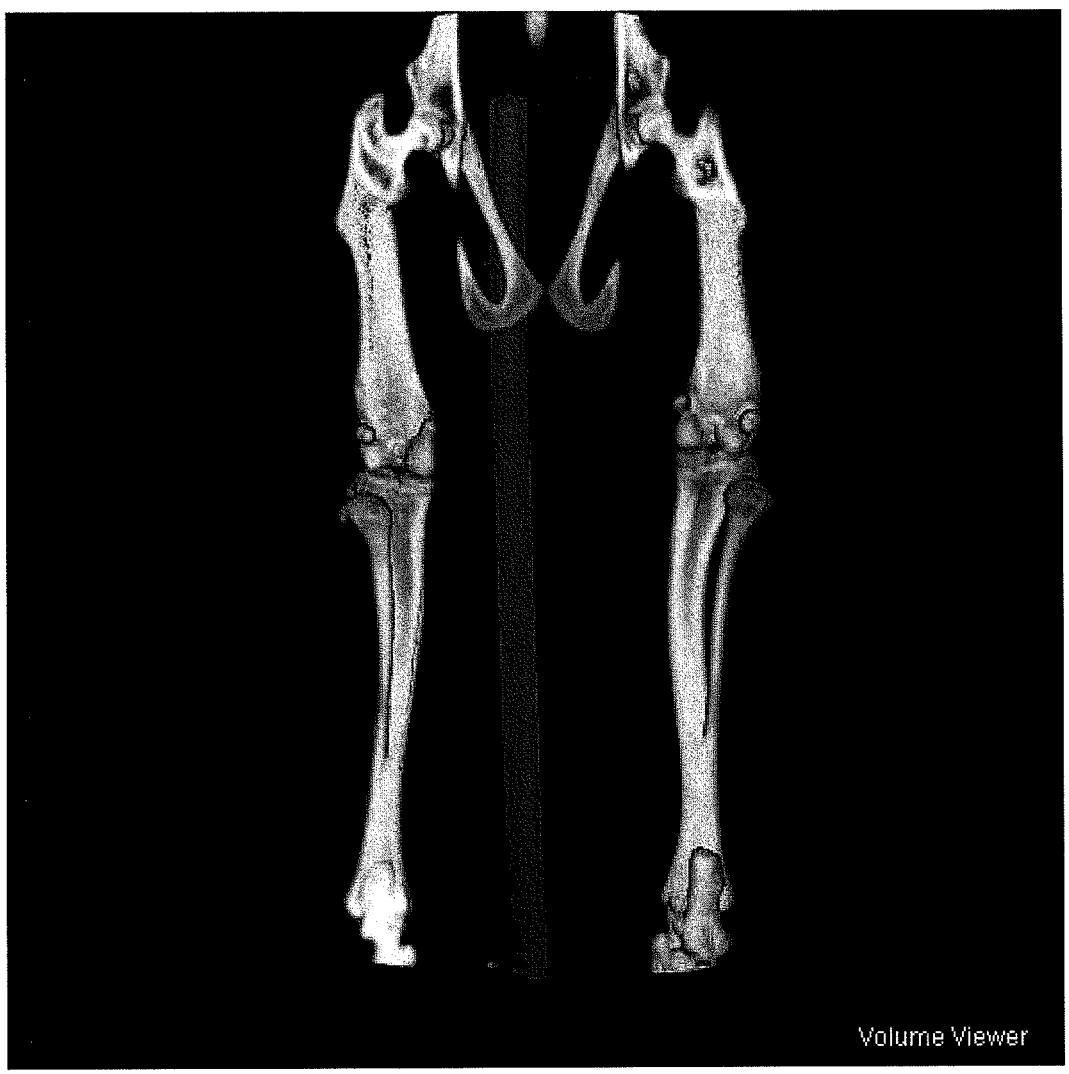
FIG. 12. 3D model of a mouse prior to injection with AuNP-DG constructed from the CT images obtained immediately before the injection. No tumor can be visualized.
Figure 13:
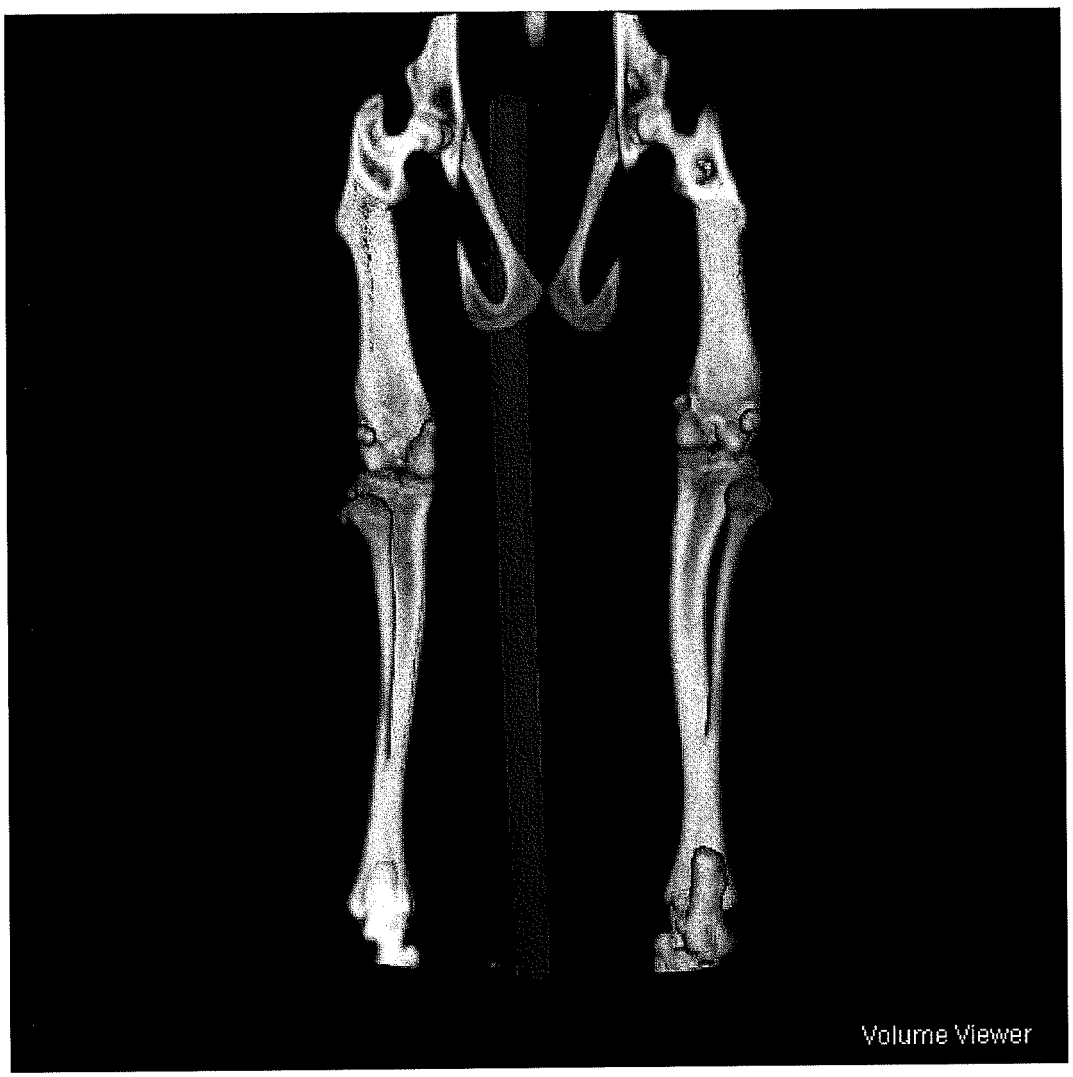
FIG. 13. 3D model of the mouse of FIG. 12, 1 hour after injection with AuNP-DG. The 3D model was created from the axial CT images obtained 1 hour post-injection. The tumor can now be clearly visualized with the help of the attenuating gold nanoparticles, which create a contrast difference between the normal and cancerous tissues.

A 3D model of a mouse prior to injection with AuNP-DG constructed from the CT images obtained immediately before the injection (FIG. 12). No tumor could be visualized prior to administration of the contrast agent. A 3D model of a mouse at one hour post-injection with AuNP-DG was created from the axial CT images obtained (FIG. 13). The tumor could now be clearly visualized due to the ability of the injected gold nanoparticles to create a greater contrast difference between the normal and cancerous tissue.

In another set of experiments, PEGylated AuNP-DG nanoparticles were administered to mice. The beads were prepared as follows. The PEGylation was carried out with methoxy PEG sulfhydryl (molecular weight 2K Dalton), which readily attaches to the surface of gold nanoparticles under room temperature in aqueous suspension via the mercapto group. The majority of PEG molecules are only terminated with mercapto groups at both ends. However, in general, around 10 PEG molecules per Au nanoparticle have a carboxyl group at the opposite end, which allows binding of 2-DG to the PEGylated nanoparticles PEGylated AuNP-DG.

We have administered mice AuNP-DG and PEGylated AuNP-DG and observed the increase in blood circulation time with the latter. This may be expected to increase the uptake rate of tumor since there will be more contrast agent available in the blood pool at any given time.

All of the compositions and methods disclosed and claimed herein can be made and executed without undue experimentation in light of the present disclosure. While the methods and compositions have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Publn. 2010/0034735
Ambrose and Hounsfield, *Br. J. Radiol.*, 46:1016-47, 1973.
Bonvento et al., *Acad. Radiol.*, 13:979-85, 2003.
Cai et al., *Invest. Radiol.*, 42:797-806, 2007.
Froman et al., *Acad. Radiol.*, 1:151-3, 1994.
Gao et al., *Nat. Biotechnol.*, 22(8):969-976, 2004.
Hainfeld et al., *Br. J. Radiol.*, 79(939):248-253, 2006.
Hayat, In: *Colloidal gold: Principles, Methods and Applications*, San Diego, Academic Press, 1990.
Hayat, In: *Colloidal Gold: Principles, Methods and Applications*. Volume 1, Academic Press, 1991.
Hayat, In: *Principles and techniques of electron microscopy, Biological applications*, London, New York, Cambridge University Press, 2000.
Hermanson, *Bioconjugate Techniques*, 2nd Ed., Elsevier/Academic Press, 2008.
Jain et al., *Mol. Pharm.*, 2(3):194-205, 2005.
Kao et al., *Acad. Radiol.*, 10:475-83, 2003.
Kim et al., *J. Am. Chem. Soc.*, 129:7661-65, 2007.
Koster and Klumperman, *Nat. Rev. Mol. Cell. Biol.*, Suppl: SS6-10, 2003.
Lee, *Trends in Biotech.*, 20:S3-S10, 2002.
Miyamoto et al., *Em. Radiol.*, 16:1050-3, 2006.
Popovtzer et al., *Nano Lett.*, 8(12):4593-4596, 2008.
Qian et al., *Nat. Biotechnol.*, 26:83-90, 2008.
Rabin et al., *Nat. Mater.*, 5:118-22, 2006.
Remington's Pharmaceutical Sciences, 18th Ed. Mack Printing Company, 1289-1329, 1990.
Schmiedl et al., *Acad. Radiol.*, 6:164-9, 1999.
Slot and Geuze, *Em. J. Cell Biol.*, 38:87-93, 1985.
Su et al., *Clin. Cancer Res.*, 12:5659-67, 2006.
Vera and Mattrey, *Acad. Radiol.*, 9:784-92, 2002.
Weissleder, *Science*, 312:1168-71, 2006.
Yu and Watson, *Chern. Rev.*, 99:2352-78, 1999.
Zhang et al., *Clin. Invest. Med.*, 31(3):E160-7, 2008.

What is claimed is:

1. A composition comprising:
    a gold nanoparticle;
    a glucose derivative comprising 2-Deoxy-D-Glucose attached to the gold nanoparticle,
    wherein the 2-Deoxy-D-Glucose is attached to the gold nanoparticle at the 2-Carbon site of the 2-Deoxy-D-Glucose.

2. The composition of claim 1, where the 2-Deoxy-D-Glucose is attached to the gold nanoparticle by a mercapto group.

3. A kit comprising:
a container having a sterile reservoir; and
a composition of claim 1 sealed in the sterile reservoir.

4. A method of preparing a subject for imaging, the method comprising administering a composition of claim 1 to the subject.

5. A method of imaging at least a portion of a subject, the method comprising:
collecting imaging data of a subject with penetrating radiation after a composition of claim 1 has been administered to the subject.

6. The method of claim 5, where collecting imaging data comprises imaging the subject with a CT scanner.

7. A method comprising: treating a subject based on imaging data collected with penetrating radiation after a composition of claim 1 has been administered to the subject.

8. An imaging contrast agent comprising:
x-ray-opaque nanoparticles; and
a deoxyglucose derivative comprising 2-Deoxy-D-Glucose attached to the nanoparticles,
wherein the 2-Deoxy-D-Glucose is attached to the nanoparticles at the 2-Carbon site of the 2-Deoxy-D-Glucose.

9. A method of making an imaging contrast agent, the method comprising:
subjecting a plurality of mercapto groups in the 2-carbon position and a plurality of gold nanoparticles (AuNP) to a condensation reaction of 2-amino-deoxyglucose and mercaptosuccinic acid.

10. A modified gold nanoparticle comprising a gold core and a surface thereon, wherein said surface comprises thioglucose, and the thioglucose is attached to the gold nanoparticle at the 2-Carbon site of the thioglucose.

* * * * *